USOO5634501A

United States Patent [19]
Walshe

[11] Patent Number: 5,634,501
[45] Date of Patent: Jun. 3, 1997

[54] DISINFECTION OF CONTAINERS

[75] Inventor: John J. Walshe, Malmesbury, England

[73] Assignee: A. G. (Patents) Limited, London, England

[21] Appl. No.: 256,658

[22] PCT Filed: Jan. 15, 1993

[86] PCT No.: PCT/GB93/00089

§ 371 Date: Nov. 23, 1994

§ 102(e) Date: Nov. 23, 1994

[87] PCT Pub. No.: WO93/13880

PCT Pub. Date: Jul. 22, 1993

[30] Foreign Application Priority Data

Jan. 15, 1992 [GB] United Kingdom .................. 9200761

[51] Int. Cl.⁶ ........................................... B08B 9/00
[52] U.S. Cl. ........................ 141/92; 141/196; 141/4;
 141/83; 141/95; 134/113; 137/241; 422/26;
 422/119
[58] Field of Search ........................ 141/1, 4, 91, 92,
 141/196, 197, 83, 89, 95; 134/113; 137/238,
 241; 422/26, 119

[56] References Cited

U.S. PATENT DOCUMENTS 1,624,573 4/1927 Bagby .................................. 137/241 X
3,648,742 3/1972 Beech .................................. 141/92
3,791,425 2/1974 Bowring ............................... 141/92
4,319,612 3/1982 Golding ................................ 141/1
4,865,814 9/1989 Childress ............................. 422/116
4,892,705 1/1990 Sternfeld et al. ................... 422/26
4,989,649 2/1991 Weiler et al. ....................... 141/1
5,124,125 6/1992 Brent .................................. 422/21
5,270,948 12/1993 O'Brien et al. ..................... 364/550

OTHER PUBLICATIONS

Soviet Inventions Illustrated, Section CH, Week 8605, Mar. 12, 1986 Derwent Pub. Ltd., London GB,–Abstract of SU1,168,184 Jul. 23, 1985.

Primary Examiner—J. Casimer Jacyna
Attorney, Agent, or Firm—Charles E. Baxley, Esq.

[57] ABSTRACT

A method and related apparatus for monitoring steam conditions in a container, such as a beer keg, during disinfection, usually in a washer/racker. Temperature and pressure are taken repeatedly within the container during the disinfection process. Resulting temperature and pressure values are inputted to a data processor. The data processor establishes automatically whether the measured temperature and pressure values correspond to desired steam conditions within the container. These conditions are at, or within a predetermined tolerance from, a phase boundary between steam and water. An output is provided which includes a direct indication of whether the desired conditions are or have been met for measuring pairs of temperature and pressure values.

29 Claims, 3 Drawing Sheets

/ 1

DISINFECTION OF CONTAINERS

FIELD OF THE INVENTION

The present invention relates to the disinfection of containers, and in particular, but not exclusively, to the steam disinfection of beer kegs in a kegging plant.

In a brewery, kegs are usually filled with beer using a piece of equipment commonly called a washer/racker. Empty kegs are positioned successively at one end of the washer/racker and pass sequentially through a series of stations or cycles where different operations are performed on the kegs. Typically the kegs pass through a number of cleaning treatments and a steam disinfection cycle before they are filled. The disinfection of the keg is of paramount importance in maintaining hygiene in the filling procedure and maintaining product quality. Disinfection is required to destroy any spoiling organisms which may remain in the keg from its previous usage and is most commonly effected using steam. High temperature, saturated steam is introduced into the keg for a given period of time to effect the disinfection.

Up to now verification of sterility has been effected by introducing a sterile solution into a keg after it is put through the washing and disinfecting cycle and retrieving the solution from the keg. The solution is then analyzed in a laboratory to detect the presence of any viable spoiling organism or other microbiological contaminants. This process is both time consuming and expensive because it requires the use of skilled personnel. Moreover it is not entirely satisfactory because the sterile solution can become contaminated by external organisms or impurities from the air. Results of the tests may take several days to process, in which time many hundreds or thousands of kegs will have been processed. There thus is a need for a method and means by which disinfection conditions inside a keg can be quickly and reliably verified.

In steam disinfection, the sanitizing effect is due to the release of latent heat on the condensing of the steam to water on the surfaces of the keg. Steam at around 100° C. can provide approximately 6 times more total heat than water at approximately the same temperature. It is found that the disinfection is most effective using steam which is at or very close to the phase boundary. At temperatures below the phase boundary temperature the steam is already condensed and will not release latent heat on the surfaces of the keg, while at temperatures significantly in excess of the phase boundary the steam is super-heated and behaves like dry heat. Dry heat requires higher temperatures and longer contact times to sanitize compared to moist heat. The temperature at which the phase boundary between water and steam occurs is itself dependent on the pressure within the keg (FIG. 4). Accordingly for optimum disinfection, we have found that the steam temperature within the keg should be at or slightly above the phase boundary temperature appropriate for the pressure within the keg and that these conditions should be maintained for a given period of time.

SUMMARY OF THE INVENTION

From a first aspect the invention provides a method of monitoring steam conditions in a container during disinfection comprising the steps of:

a) repeatedly taking measurements of the temperature and pressure within the container during disinfection;

b) inputting measured temperature and pressure values to data processing means;

c) establishing automatically in said processing means whether measured temperature and pressure values correspond to desired steam conditions within the container, such conditions being at or within a predetermined tolerance from the phase boundary between steam and water; and d) providing an output including a direct indication of whether the desired conditions are or have been met for measured pairs of temperature and pressure values, preferably for each successively measured pair.

From a second aspect the invention provides apparatus for monitoring the steam conditions in a container during disinfection comprising:

a) means for measuring the temperature and pressure within a container during disinfection;

b) data processing means;

c) means for inputting said temperature and pressure values into said data processing means, said processing means establishing automatically whether the measured temperature and pressure values correspond to desired steam conditions within the container, such conditions being at or within a predetermined tolerance from the phase boundary between steam and water; and d) output means for providing a direct indication of whether the desired conditions are or have been met for measured pairs of temperature and pressure values, preferably for each successively measured pair.

Thus, in accordance with the invention, the measured process conditions are continually and automatically compared with the desired conditions of saturated steam and if such are satisfactory a direct indication to this effect is produced by the data processing means.

Preferably, the processing means operates by taking, for each simultaneous temperature and pressure measurement, the value of one parameter as a reference value, and establishing a target value for the other parameter representative of phase boundary conditions within the container, comparing the measured value of the other parameter against the target value, and, if said measured value is within a pre-determined range from said target value, providing said output.

If temperature is taken as a reference value, the measured pressure may be compared with the target pressure which would provide saturated steam (ie. the phase boundary condition) at the measured temperature and the indication given if the measured pressure is within a pre-determined range of the saturated steam pressure. Preferably, however pressure is used as the reference value and the measured temperature compared with a target steam saturation temperature.

The processing means may function by calculating the target values, although it preferably is provided with pre-stored such values corresponding to particular values of the reference parameter.

Preferably the time at which the pairs of readings are taken is measured, calculated or recorded and input to the data processing means, and preferably the measured temperature and/or pressure is displayed on a screen and/or printed, in graphical form, against time. Pressure and temperature measurement may be superimposed on one graph suitably distinguished (for example by color) or as two separate graphs. Preferably the temperature measurements at least are displayed, and a pre-determined minimum critical disinfection temperature is also preferably displayed as a reference line on the temperature graph so that a person interpreting the graph may immediately see that the temperature has exceeded the minimum temperature.

In one embodiment, the data processing means also compares each measured temperature value against a predetermined minimum disinfection temperature, the desired output indication only being given if the measured temperature is above this minimum temperature and if the pressure and temperature conditions are within the permitted tolerance.

Where results are displayed graphically, the direct indication that the disinfection conditions are within the given tolerance may be presented by altering the visual appearance of the temperature and/or pressure plot, for example by changing its color. Other visual means could be employed for example presenting the plot as dotted for example, if the correct conditions exist.

Thus a person studying the graph will be able to tell at a glance the time for which the correct disinfection conditions existed, and compare this to a predetermined minimum time, to assess whether or not the whole process has been satisfactory. Thus, the preferred display means are advantageous and represent a new departure from the prior art.

This minimum time period may be stored by the data processing means which may either instead of, or in addition to, presenting the temperatures etc graphically, produce a suitable message to indicate that the disinfection was successful if the disinfection temperature was above the predetermined minimum and saturated steam conditions existed for the minimum time period.

As mentioned above, the satisfactory steam conditions are assessed if a measured value lies within a given tolerance of the phase boundary condition. To establish the desired phase boundary condition the data processing means may include memory means which store tables of saturated steam conditions over a given range of temperatures and pressures. The measured temperature value, for example, may then be compared against the saturated steam target temperature at the measured pressure and the output indication given if it lies within a given tolerance of said saturated steam value. Preferably this tolerance is 0° C. to +3° C., although preferably the data processing means may be adapted so that this tolerance can be altered as required. Furthermore, preferably the data processing means is adapted such that the table is not applied to temperatures measured below a pre-determined threshold value, for example 100° C.

Measurement of pressure and temperature may be taken at convenient time intervals, for example every half second.

Preferably the invention is applied to the disinfection of kegs in a kegging line. In such a process, the pressure and temperature within a keg may be measured throughout the whole kegging procedure although this is not essential. In a preferred embodiment of the invention, therefore, a test keg is provided which comprises means for continuously measuring the internal pressure and temperature of the keg. The measured pressure and temperature data may be stored in memory means mounted on the keg and the information downloaded to the data processing means at the end of the kegging procedure. Thus in a preferred embodiment the keg comprises data storage means and data transfer means. The data transfer means may comprise direct contact means, for example a plug or socket arrangement or remote means, for example radio or other transmission means.

In a further embodiment the temperature and pressure measurements may be transmitted directly from the test keg to the data processing means during the disinfection procedure and, if the disinfecting parameters are outside the desired envelope, a correction may be applied to the disinfecting procedure automatically by way of feedback. Such an arrangement would not necessarily comprise the output means of the first and second aspects of the invention, because a correction may be made without user intervention.

Thus from a third aspect the invention provides a method of monitoring steam conditions in a container during disinfection comprising the steps of:

a) repeatedly taking measurements of the temperature and pressure within the container during disinfection;

b) inputting measured temperature and pressure values to data processing means;

c) establishing automatically in said processing means whether measured temperature and pressure values correspond to desired steam conditions within the container, such conditions being at or within a predetermined tolerance from the phase boundary between steam and water; and d) if said measured values do not fall within the predetermined tolerance, providing an output for use in automatically correcting the disinfection process.

From a fourth aspect the invention also provides apparatus for monitoring the steam conditions in a container during disinfection comprising:

a) means for measuring the temperature and pressure within a container during disinfection;

b) data processing means;

c) means for inputting said temperature and pressure values into said data processing means, said processing means establishing automatically whether the measured temperature and pressure values correspond to desired steam conditions within the container, such conditions being at or within a predetermined tolerance from the phase boundary between steam and water, and, if said desired steam conditions are not met, providing an output for use in controlling the disinfection apparatus.

As mentioned above the recording of pressure and temperature may be effected throughout the kegging procedure or merely during selected parts thereof. Means may therefore be provided automatically to start and stop the data recording. Furthermore since in a brewery there will be many individual kegging lanes, means may be provided to identify the particular lane for which the measurements have been taken. In one embodiment this may be by means of a rotary switch, for example, which is set by an operator to a pre-determined position before commencing the disinfecting procedure, but this could be performed automatically by suitable means arranged on the keg or kegging lane.

It will be appreciated that the present invention will also allow for easy maintenance of records of disinfection conditions because pressure and temperature readings may be output in graphical form or in the form of tables from the data processing means. Furthermore the data may be exported to other systems, for example control or monitoring systems.

Furthermore the keg used may monitor other parameters in the line, for example the detection of the presence or concentration of air, $CO_2$, nitrogen or other specific gases, the relative humidity, the pH, and acceleration of the keg.

Switch means may also be provided to indicate when the keg is clamped at a station in the racker. For example switch means on the keg may be activated by a clamping plate or bar co-operating therewith or a proximity switch be operated thereby. The various washing and racking cycles take place after the keg is clamped at the appropriate station and the periods for which clamping occurs are of interest because if a keg remains at a station for too long, cycle times may be increased unnecessarily. The switch state may be recorded on the keg along with the other data measurements and may be later indicated graphically. For example, a vertical line of one color may be produced on the graph showing temperatures and pressures to indicate that a keg has been clamped at a particular station, and a vertical line of a different color produced to show when the clamping is released. This will allow an operator to determine the length of time a keg is clamped at a given station.

It will also be appreciated that the direct indication that desired sterilization conditions are being or have been met over the sterilization cycle or at one or more points in the cycle can be non-graphical.

BRIEF DESCRIPTION OF THE DRAWINGS

A preferred embodiment of the invention will now be described, by way of example only, with reference to the accompanying drawings in which.

DESCRIPTION OF THE PREFERRED EMBODIMENT

Figure 1:
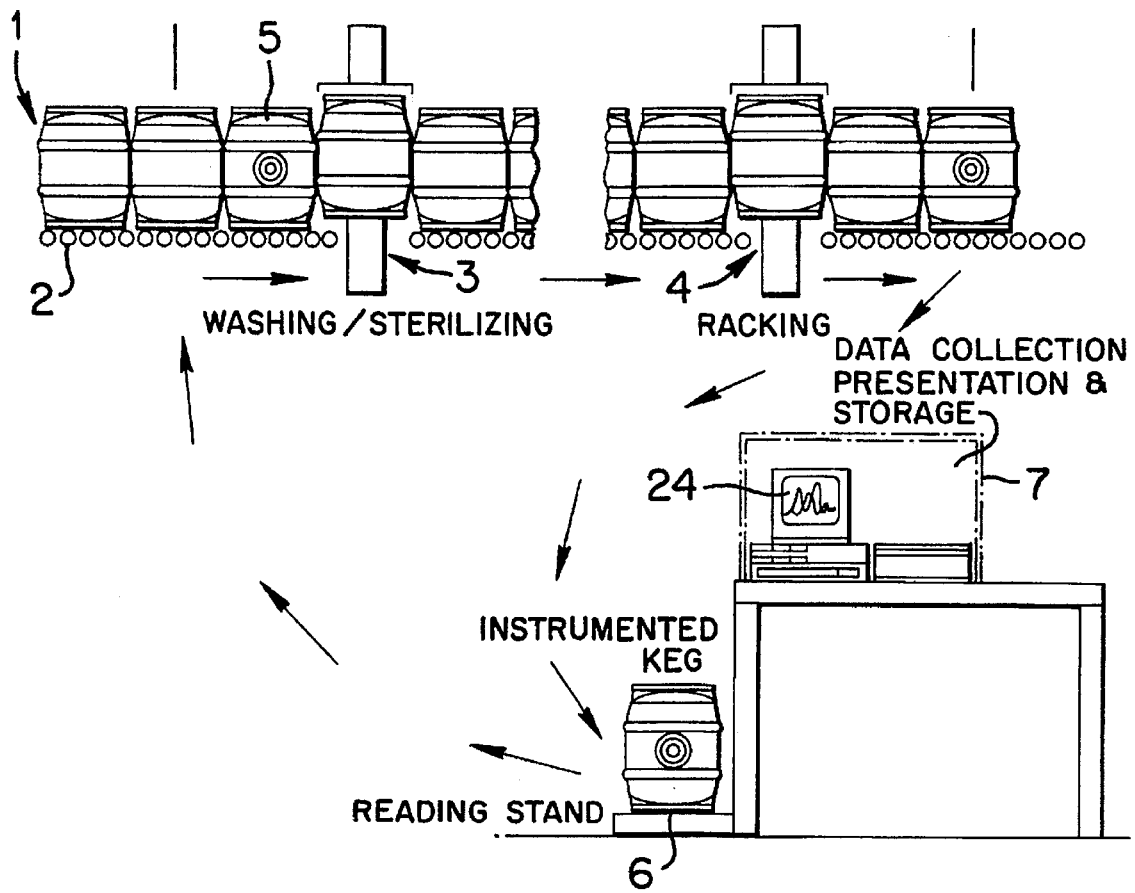
FIG. 1 is a flow diagram illustrating the disinfecting data collection and transfer to data processing means using an instrumented test keg.
Figure 4:
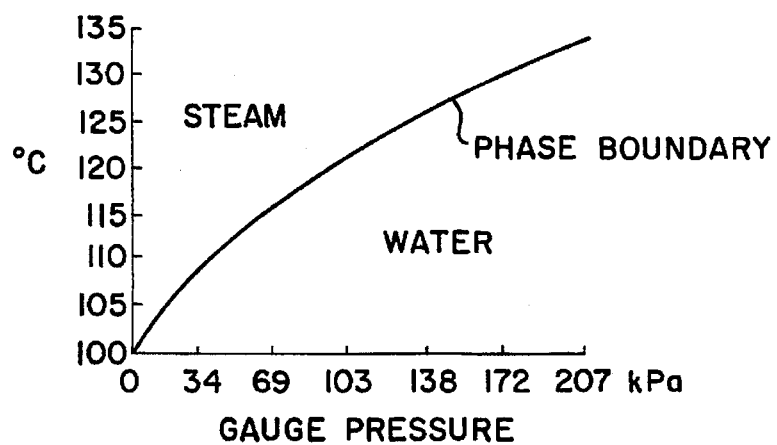
FIG. 4 is a steam/water phase transition graph.

Referring firstly to FIG. 1, the passage of kegs along a kegging line is illustrated diagrammatically. Kegs 1 pass along the line 2 and pass sequentially through a number of washing stations and then to a disinfecting station 3. After disinfection, the kegs are filled at a filling station 4 whereafter they are removed from the end of the line for despatch.

A test keg 5 is placed on the line for the measurement of pressure and temperature within the keg as it passes along the line 1. The temperature and pressure data and the time from the commencement of measurement of the data are stored on the keg which, after reaching the end of the line, is removed to a reading station 6 where the data is transferred to a data processor 7a for analysis.

Figure 2:
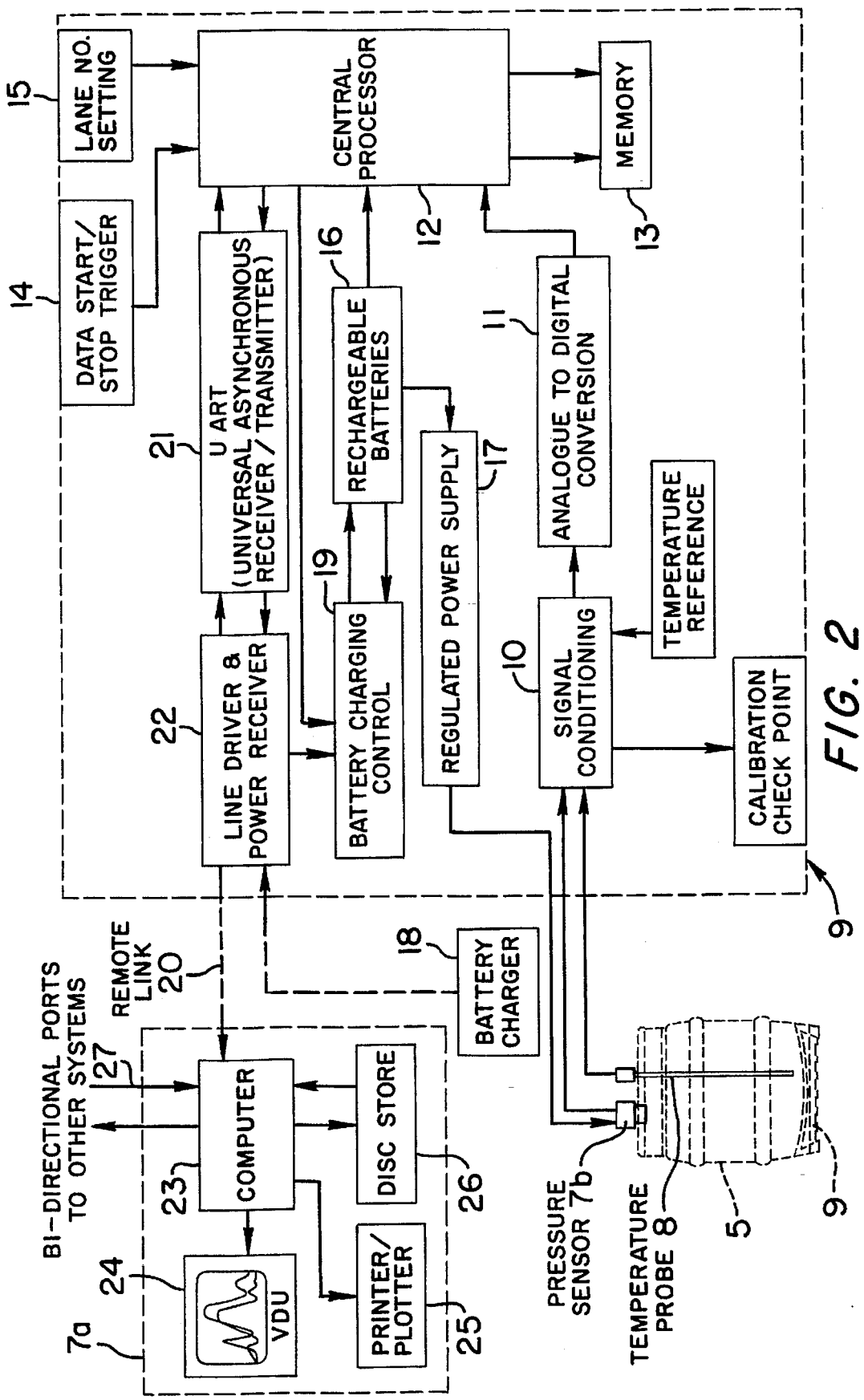
FIG. 2 shows schematically, further details of the test keg and data processing means.

Referring to FIG. 2, the test keg 5 is essentially a standard keg, which is fitted with a pressure sensor 7b and a temperature sensor 8 arranged within the keg at suitable positions. The sensors are connected to a unit 9 arranged externally in the bottom space of the keg 5. The unit 9 contains electronic equipment for measuring and storing the readings taken by the sensors 7b, 8. The signals produced by the pressure and temperature sensors pass through signal conditioning means 10 and through an analogue to digital converter 11 before entering a central processor 12. The processor processes the signals from the sensors and inputs to memory means 13 the pressure and temperature readings taken. Pressure and temperature readings are stored every ½ second.

Also inputted to the central processor 12 may be signals from means 15 for indicating the particular line from which the temperature and pressure measurement have been taken. The means 15, for example, comprise a multiple setting switch fitted to the keg, or other means for producing a signal indicative of the line number, which is input to the processor at the beginning of the run.

Means 14 may also be provided which initiate or terminate the taking of readings. These means may for example comprise a photosensor provided externally of the keg which is activated at the start and finish of the process cycle.

The sensors and central processor may be powered by rechargeable batteries 16 mounted on the keg. The pressure and temperature sensors are supplied through a regulator 17. The batteries 16 will be recharged by a battery charger 18 via a power receiving port and a charging control 19 when the keg is placed on the stand 6.

In the embodiment shown the pressure and temperature data stored in memory 13 are transferred to the data processing means 7a when the keg 5 is placed on the stand 6, via a remote link 20, for example through an induction coil system. Of course the data may be transferred through simple plug and socket connectors if desired. Signals from the central processor 12 pass through a receiver/transmitter 21 and line driver 22 for transmission to the data processing means 7a.

The data processing means comprises a computer 23. The computer 23 has, in memory, tables of saturated steam conditions, the pre-determined minimum disinfection temperature and the pre-determined allowable tolerance of measured parameters compared to saturated steam conditions. The computer 23 may display the pressure and temperature measurements taken in the keg in graphical form on a screen 24 or output the information to a printer/plotter 25 or a disk storage means 26.

Figure 3:
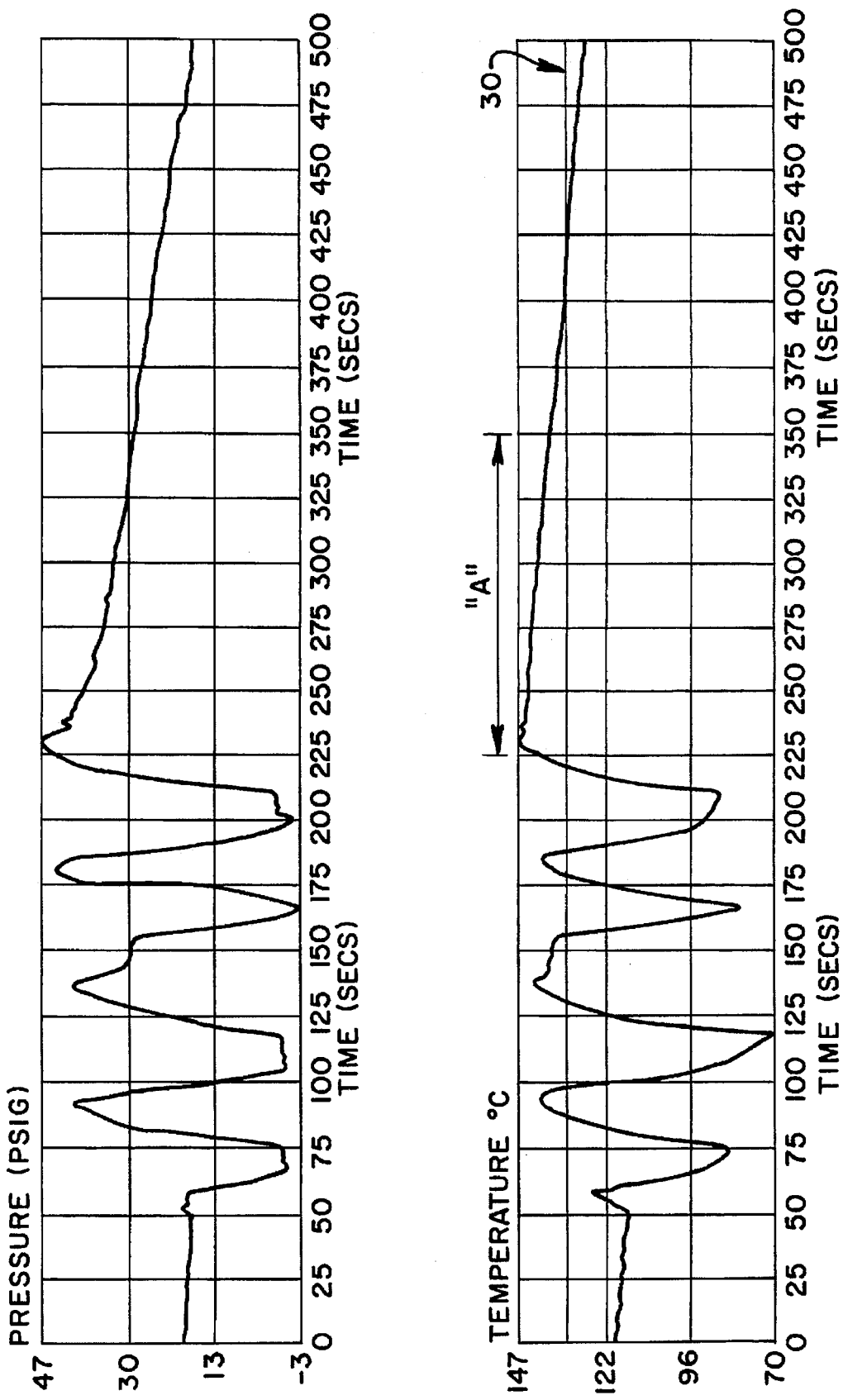
FIG. 3 shows typical output from the data processing means.

A typical plot of measured temperature and pressure against time is shown in FIG. 3. These graphs may be superimposed one upon the other if desired, as shown schematically in FIG. 2. In this particular embodiment, the minimum disinfection temperature (regardless of pressure) is 132° C. and the computer produces a line 30 on the temperature plot showing this pre-determined, minimum temperature value.

For each pair of pressure and temperature measurements taken, the computer takes the pressure measurement as a reference value, and obtains from the stored steam tables a target temperature of saturated steam (i.e. the phase boundary condition) at that pressure. It then compares the measured temperature with that temperature and if the measured temperature lies within a tolerance band of 0° to +3° C., the computer changes a visual characteristic, for example the color of the temperature and/or the pressure plot (which may be superimposed one upon the other). To ensure satisfactory disinfection, the saturated steam conditions should pertain for a given minimum period of time, for example 1 minute. In the graph shown in FIG. 3, the disinfection procedure commences at about 210 seconds from the start of the recording of data. It will be seem that the pressure and temperature rise rapidly to maximum values at around 230 seconds whereafter they tail off. The operator interpreting the results of the test run will be able to observe at a glance from the temperature plot that the temperature during disinfection has been above the pre-determined minimum value, by reference to the line 30, and also that the desired steam conditions have pertained for the minimum period by reference to the color of the temperature plot over the relevant range. In the plot of FIG. 3 it might be expected that the portion "A" of the plot would be of a different color to the rest of the plot, for example.

The presence of acceptable steam conditions could be indicated in a manner other than the change of color of the temperature plot. For example the line could be presented in a dotted manner where the conditions exist and as solid elsewhere, or vice-versa. Furthermore if, in addition the minimum time period is programmed into the processing means the processing means could merely give a pass or fail indication which would indicate whether during that minimum time period the steam conditions were acceptable, and that the temperature was above the minimum value.

Should the plot indicate that the disinfection conditions are not within desired boundaries then the disinfecting apparatus may be adjusted accordingly.

It will be appreciated that the pressure and temperature data (and any other data which may be collected by the keg during its passage along the line) may be stored for subsequent use, for example in quality control procedures. Furthermore while the invention has been described with reference to disinfecting kegs it could also be applied to other types of container.

While the preferred embodiment described gives an indication that the desired disinfection conditions have been met, it will be appreciated that it may be adapted so as to provide an output for use in automatically controlling the disinfection apparatus. The computer 23 may thus provide outputs for this or other systems for example via ports 27.

I claim:

1. A method of monitoring steam conditions in a container during disinfection comprising the steps of:
   a) repeatedly taking measurements of the temperature and pressure within the container during disinfection;
   b) inputting measured temperature and pressure values to data processing means;
   c) establishing automatically in said processing means whether measured temperature and pressure values correspond to desired steam conditions within the container, such conditions being at or within a predetermined tolerance from a phase boundary between steam and water, by taking, for each simultaneous temperature and pressure measurement, the value of one parameter as a reference value, and establishing a target value for the other parameter representative of phase boundary conditions within the container, comparing the measured value of the other parameter against the target value, and determining if said measured value is within a predetermined tolerance from said target value; and
   d) providing an output including a direct indication of whether the desired conditions are or have been met for measured pairs of temperature and pressure values if said measured value is within said predetermined tolerance from said target value.

2. A method as claimed in claim 1 wherein pressure is used as the reference value and the measured temperature compared with a target steam saturation temperature.

3. A method as claimed in claim 2 wherein the indication is given if the measured temperature is within a tolerance of 0° to +3° C. of the saturated steam temperature.

4. A method as claimed in claim 1 wherein said target values are pre-stored in said data processing means.

5. A method as claimed in claim 1 wherein the time at which the pairs of readings are taken is measured, calculated or recorded and input to the data processing means, and the measured temperature and/or pressure is displayed on a screen and/or printed, in graphical form, against time.

6. A method as claimed in claim 5 wherein the temperature measurements at least are displayed, and a predetermined minimum critical disinfection temperature is also displayed as a reference line on the temperature graph.

7. A method as claimed in claim 5 wherein the direct indication that the disinfection conditions are within the given tolerance is effected by altering the visual appearance of the temperature and/or pressure plot.

8. A method as claimed in claim 7 wherein the colour of said plot is changed.

9. A method as claimed in claim 1 wherein the data processing means compares each measured temperature value against a predetermined minimum disinfection temperature, the desired output indication only being given if the measured temperature is above this minimum temperature and if the pressure and temperature conditions are within the permitted tolerance.

10. A method as claimed in claim 1 wherein said container is a beer keg having means for measuring the temperature and pressure within the keg.

11. The method as claimed in claim 10, wherein the measured data is stored in memory means for storing date provided on the keg and the information is downloaded to the data processing means at the end of the kegging procedure.

12. A method as claimed in claim 1, wherein said container has means for measuring the temperature and pressure within the container, the measured data is stored in memory means for storing data provided on the container, and the information downloaded to the data processing means during or at the end of the disinfection procedure.

13. A method of monitoring steam conditions in a container during disinfection comprising the steps of:
   a) repeatedly taking measurements of the temperature and pressure within the container during disinfection;
   b) inputting measured temperature and pressure values to data processing means;
   c) establishing automatically in said processing means whether measured temperature and pressure values correspond to desired steam conditions within the container, such conditions being at or within a predetermined tolerance from the phase boundary between steam and water; and
   d) providing an output including a direct indication of whether the desired conditions are or have been met for measured pairs of temperature and pressure values;
   wherein said container is a beer keg having means for measuring temperature and pressure within the keg and wherein the measured data is stored in memory means for storing data provided on the keg and the information downloaded to the data processing means at the end of the kegging procedure.

14. Apparatus for monitoring the steam conditions in a container during disinfection comprising:
   a) means for measuring the temperature and pressure within a container during disinfection;
   b) data processing means;
   c) means for inputting said temperature and pressure values into said data processing means, said processing means comprising means for establishing automatically whether the measured temperature and pressure values correspond to desired steam conditions within the container, such conditions being at or within a predetermined tolerance from a phase boundary between steam and water, comprising means for establishing a target value for one parameter representative of phase boundary conditions within the container from the measured other parameter, and comparing the measured one parameter against the target value, and determining if said measured value is within a predetermined tolerance from said target value; and
   d) output means for providing a direct indication of whether the desired conditions are or have been met for measured pairs of temperature and pressure values if said measured value is within said predetermined tolerance from said target value.

15. Apparatus as claimed in claim 14 comprising storage means for pre-storing said target values.

16. Apparatus as claimed in claim 14 comprising means for determining the time at which pairs of readings are taken and means for displaying at least some of said readings graphically against time.

17. Apparatus as claimed in claim 16 comprising means for displaying the measured temperatures graphically and for superimposing on said graph a line representative of a minimum disinfection temperature.

18. Apparatus as claimed in claim 16 comprising means for changing the visual appearance of the graph when the desired conditions have been met.

19. Apparatus as claimed in claim 18 comprising means for changing the colour of the graph when the desired conditions have been met.

20. Apparatus as claimed in claim 14 wherein said data processing means comprises a computer.

21. Apparatus as claimed in claim 14 comprising means mounted on the container for storing said measured pressure and temperature data and means for transferring said data to said data processing means after completion of the taking of readings.

22. Apparatus as claimed in claim 14 wherein said container is a beer keg.

23. Apparatus as claimed in claim 14 comprising means for starting and stopping automatically the recording of data.

24. Apparatus as claimed in claim 14, wherein said means for measuring the temperature and pressure within the container are mounted on the container, said apparatus further comprising memory means for storing data mounted on the container for storing the measured data, and means for downloading the information to the data processing means during or at the end of the disinfection procedure.

25. A method of monitoring steam conditions in a container during disinfection comprising the steps of:
   a) repeatedly taking measurements of the temperature and pressure within the container during disinfection;
   b) inputting measured temperature and pressure values to data processing means;
   c) establishing automatically in said processing means whether measured temperature and pressure values correspond to desired steam conditions within the container, such conditions being at or within a predetermined tolerance from a phase boundary between steam and water, by taking, for each simultaneous temperature and pressure measurement, the value of one parameter as a reference value, and establishing a target value for the other parameter representative of phase boundary conditions within the container, comparing the measured value of the other parameter against the target value, and determining if said measured value is within a predetermined tolerance from said target value; and
   d) if said measured value does not fall within said predetermined tolerance from said target value, providing an output for use in automatically correcting the disinfection process.

26. Apparatus for monitoring the steam conditions in a container during disinfection comprising:
   a) means for measuring the temperature and pressure within a container during disinfection;
   b) data processing means;
   c) means for inputting said temperature and pressure values into said data processing means, said processing means comprising means for establishing automatically whether the measured temperature and pressure values correspond to desired steam conditions within the container, such conditions being at or within a predetermined tolerance from a phase boundary between steam and water, comprising means for establishing a target value for one parameter representative of phase boundary conditions within the container from the measured other parameter, and comparing the measured one parameter against the target value, and determining if said measured value is within a predetermined tolerance from said target value; and means for providing an output for use in controlling the disinfection apparatus if said measured value does not fall within said predetermined tolerance from said target value.

27. A method of monitoring steam conditions in a container during disinfection comprising the steps of:
   a) repeatedly taking measurements of the temperature and pressure within the container during disinfection;
   b) inputting measured temperature and pressure values to data processing means;
   c) establishing automatically in said processing means whether measured temperature and pressure values correspond to desired steam conditions within the container, such conditions being at or within a predetermined tolerance from a phase boundary between steam and water; and
   d) providing an output including a direct indication of whether the desired conditions are or have been met for measured pairs of temperature and pressure values; wherein:
      said container is a beer keg having means for measuring the temperature and pressure within the keg, the measured data is stored in memory means for storing data provided on the keg, and the information downloaded to the data processing means at the end of the kegging procedure.

28. A method of monitoring steam conditions in a container during disinfection comprising the steps of:
   a) repeatedly taking measurements of the temperature and pressure within the container during disinfection;
   b) inputting measured temperature and pressure values to data processing means;
   c) establishing automatically in said processing means whether measured temperature and pressure values correspond to desired steam conditions within the container, such conditions being at or within a predetermined tolerance from a phase boundary between steam and water; and
   d) providing an output including a direct indication of whether the desired conditions are or have been met for measured pairs of temperature and pressure values; wherein:
      said container has means for measuring the temperature and pressure within the container, the measured data is stored in memory means for storing data provided on the container, and the information downloaded to the data processing means during or at the end of the disinfection procedure.

29. Apparatus for monitoring the steam conditions in a container during disinfection comprising:
   a) means for measuring the temperature and pressure within a container during disinfection;
   b) data processing means;
   c) means for inputting said temperature and pressure values into said data processing means, said processing means establishing automatically whether the measured temperature and pressure values correspond to desired steam conditions within the container, such conditions being at or within a predetermined tolerance from a phase boundary between steam and water; and d) output means for providing a direct indication of whether the desired conditions are or have been met for measured pairs of temperature and pressure values; wherein;

said means for measuring the temperature and pressure within the container are mounted on the container, said apparatus further comprising memory means for storing data mounted on the container for storing the measured data, and means for down loading the information to the data processing means during or at the end of the disinfection procedure.

* * * * *